United States Patent

Regen

Patent Number: 5,583,239
Date of Patent: Dec. 10, 1996

[54] ANTIMICROBIAL STEROL CONJUGATES

[75] Inventor: Steven L. Regen, Allentown, Pa.

[73] Assignee: Lehigh University, Bethlehem, Pa.

[21] Appl. No.: 452,846

[22] Filed: May 30, 1995

[51] Int. Cl.$^6$ .................... C07J 9/00; C07J 1/00
[52] U.S. Cl. ............................ 552/554; 552/636
[58] Field of Search .................. 552/636, 554

[56] References Cited

U.S. PATENT DOCUMENTS 5,122,520  6/1992  Azria et al. ................... 514/171
5,352,682  10/1994  Sipos ............................ 514/182

FOREIGN PATENT DOCUMENTS 489423   6/1992  European Pat. Off. .
624593   11/1994  European Pat. Off. .
9323041  11/1993  WIPO .
9323040  11/1993  WIPO .

Primary Examiner—Kimberly J. Prior
Attorney, Agent, or Firm—Yahwak & Associates

[57] ABSTRACT

The invention discloses steroid conjugates having the following structure:

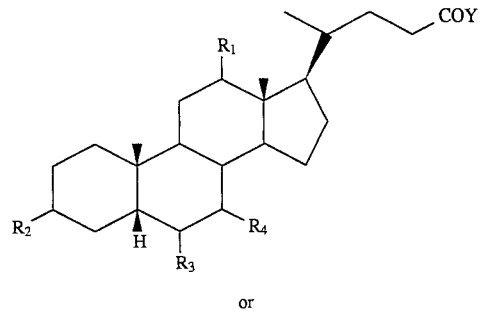

or

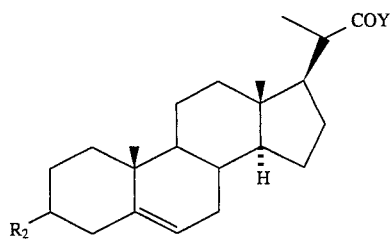

where Y is $NHCH_2CH_2CH_2CH_2NH_2$, $NH(CH_2)_3NH(CH_2)_4NH(CH_2)_3NH_2$, or $NHCH_2CH_2NHCH_2CH_2NHCH_2CH_2NH_2$, and each of $R_1$, $R_2$, $R_3$ and $R_4$ is individually H, OH and $OSO_3H$. These conjugates posses antimicrobial properties and are, therefore, useful as antibiotics.

16 Claims, No Drawings

ANTIMICROBIAL STEROL CONJUGATES

Partial financial support in the making of the invention described herein was provided by the National Institutes of Health. In view of providing financial support to the making of the invention described herein, the United States government has certain statutory interests in the invention under 35 USC 200 et seq.

In the course of studies exploring the diversity of antibiotics from animal sources, Michael Zasloff and his colleagues reported on the isolation, structural determination and antimicrobial activity of the first aminosterol antibiotic from stomach extract of the shark *Squalus acanthias* [see Proc. Natl. Acad. Sci., USA 90:1354 (1993), and U.S. Pat. No. 5,192,756]. This antibiotic was given the name "squalamine" by its discoverers since it was derived from the genus *Squalus*, and its chemical structure was that of an amine. Since its discovery, this naturally-occurring aminosterol has attracted considerable interest because of its potent antimicrobial activity against a broad spectrum of microorganisms.

Chemically, squalamine is 3β-N-1-{N-[3-(4-aminobutyl)]-1,3-diaminopropane}-7α,24ζ-dihydroxy-5α-cholestane 24-sulfate, and has the structure:

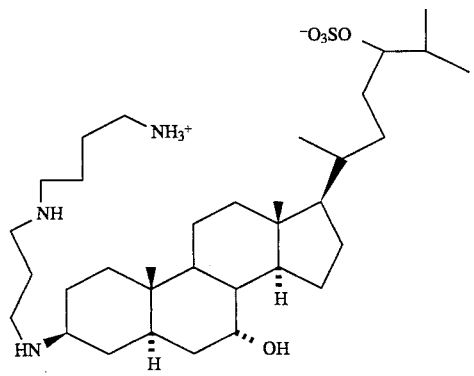

At the present, the feasibility of obtaining large quantities of this steroidal antibiotic from natural sources appears questionable since only trace amounts are present in the liver and gallbladder of the shark. While a recent synthesis [see Tetrahedron Letters 35(44):8103 (1994)] has confirmed the structure of squalamine, the 17 steps that are needed to achieve the product, together with a low overall yield (0.36%) and expensive starting material (3β-acetoxy-5-cholenic acid) makes such a route impractical for large-scale production.

Accordingly, there is a need to develop more economical procedures, both in time and cost, for the synthesis of squalamine, and that is where the research effort that led to the making of the compounds described for the first time herein, was directed. This research effort led to the discovery of two and three-step protocols that led to the synthesis of molecules generally sharing a sterol core similar to that of squalamine, but also share its extraordinary antimicrobial properties. Furthermore, the results obtained in the making of the present invention also demonstrate for the first time that the placement of a pendant polyamine (e.g., spermine) and sulfate groups on the A and D rings of a structurally related sterol may be reversed with retention of antimicrobial activity, and that much more accessible squalamine-like compounds, or "mimics", are possible.

By the term "mimic" as used in the description of the present invention is meant an aminosterol compound that contains a cholane ring core (which may be saturated or unsaturated) as found in squalamine. By the term "spermine" as used in the description of the present invention is meant an amino-organic radical having the chemical formula —$NH(CH_2)_3NH(CH_2)_4NH(CH_2)_3NH_2$.

Accordingly it is one aspect of the present invention to describe a series of novel squalamine mimics having a pendant polyamine (e.g., spermine) attached to the D ring of the molecule, and a sulfate group attached to the A ring of the molecule.

It is another aspect of the present invention to describe a protocol by which such squalamine mimics may be synthesized.

It is still another aspect of the present invention to provide data showing that the squalamine mimics according to the present invention exhibit potent antibiotic properties against a broad spectrum of microorganisms.

These and other aspects of the present invention may be more fairly understood in conjunction with the following examples and detailed description of the present invention.

Synthesis for the compounds according to the present invention begins with one of seven starting materials, all of which are commercially available. These materials are 23, 24-bisnor-5-cholenic acid-3β-ol; deoxycholic acid; cholic acid; 5β-cholanic acid; 5β-cholanic acid-3α-ol; 5β-cholanic acid-3α,6α-diol; and 5β-cholanic acid-3α,7α-diol. Structurally these materials are:

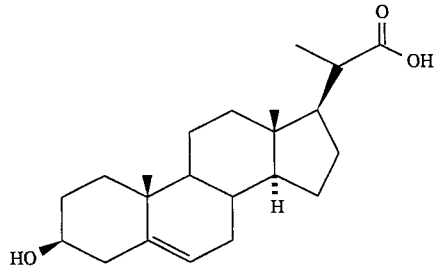

23,24-bisnor-5-cholenic acid-3β-ol

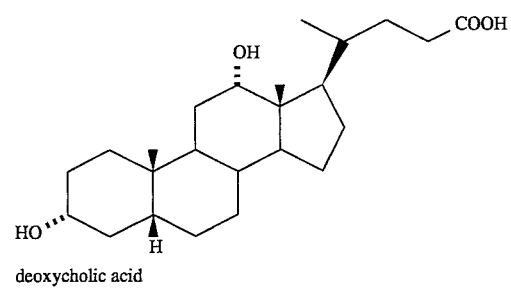

deoxycholic acid

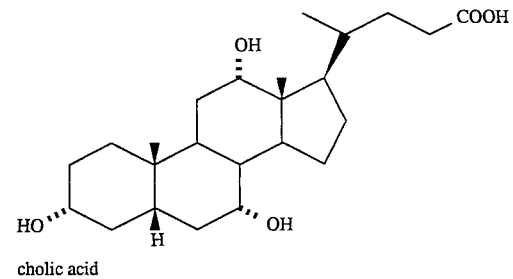

cholic acid

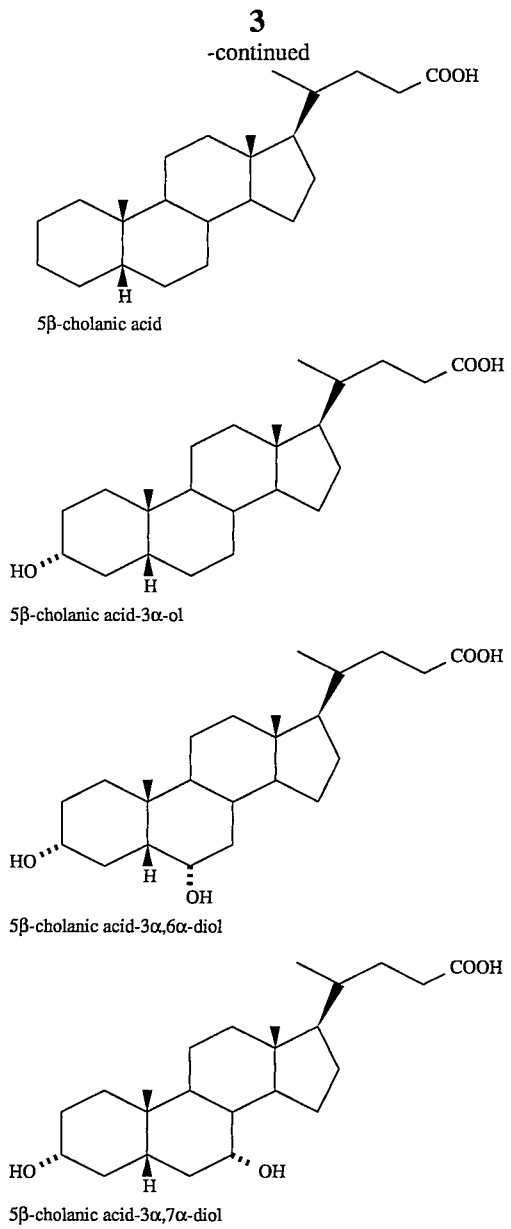

5β-cholanic acid

5β-cholanic acid-3α-ol

5β-cholanic acid-3α,6α-diol

5β-cholanic acid-3α,7α-diol

Using these materials in the appropriate protocol, compounds according to the present invention may be readily synthesized.

In its broadest interpretation, the compounds according to the present invention are those having the formulae

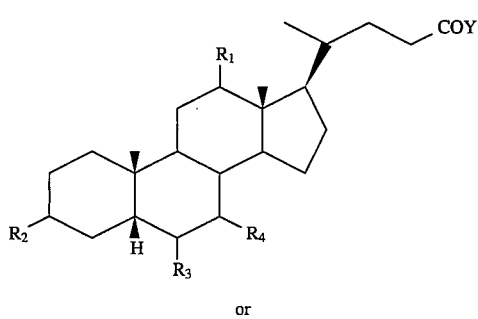

or

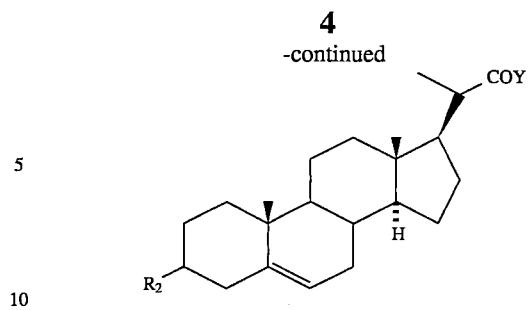

wherein each $R_1$, $R_2$, $R_3$, and $R_4$ may be H, OH or $OSO_3H$; and wherein Y is spermine, that is $NH(CH_2)_3NH(CH_2)_4NH(CH_2)_3NH_2$, $NHCH_2CH_2CH_2CH_2NH_2$, or $NHCH_2CH_2NHCH_2CH_2NHCH_2CH_2NH_2$.

More specifically, the preferred compounds according to the present invention are those having the following structures.

| Compound | X | Y |
|---|---|---|

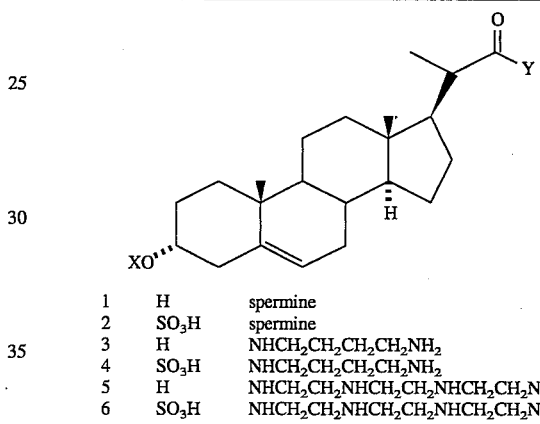

| 1 | H | spermine |
| 2 | $SO_3H$ | spermine |
| 3 | H | $NHCH_2CH_2CH_2CH_2NH_2$ |
| 4 | $SO_3H$ | $NHCH_2CH_2CH_2CH_2NH_2$ |
| 5 | H | $NHCH_2CH_2NHCH_2CH_2NHCH_2CH_2NH_2$ |
| 6 | $SO_3H$ | $NHCH_2CH_2NHCH_2CH_2NHCH_2CH_2NH_2$ |

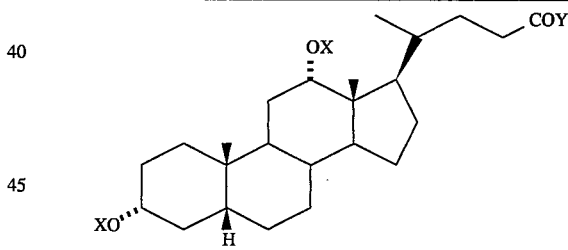

| 7 | H | spermine |
| 8 | $SO_3H$ | spermine |
| 9 | H | $NHCH_2CH_2CH_2CH_2NH_2$ |
| 10 | $SO_3H$ | $NHCH_2CH_2CH_2CH_2NH_2$ |
| 11 | H | $NHCH_2CH_2NHCH_2CH_2NHCH_2CH_2NH_2$ |
| 12 | $SO_3H$ | $NHCH_2CH_2NHCH_2CH_2NHCH_2CH_2NH_2$ |

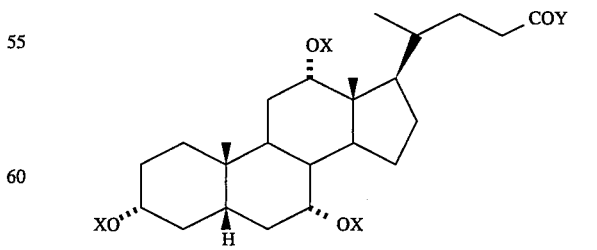

| 13 | H | spermine |
| 14 | $SO_3H$ | spermine |
| 15 | H | $NHCH_2CH_2CH_2CH_2NH_2$ |
| 16 | $SO_3H$ | $NHCH_2CH_2CH_2CH_2NH_2$ |

5

-continued

| Compound | X | Y |
|---|---|---|
| 17 | H | NHCH$_2$CH$_2$NHCH$_2$CH$_2$NHCH$_2$CH$_2$NH$_2$ |
| 18 | SO$_3$H | NHCH$_2$CH$_2$NHCH$_2$CH$_2$NHCH$_2$CH$_2$NH$_2$ |

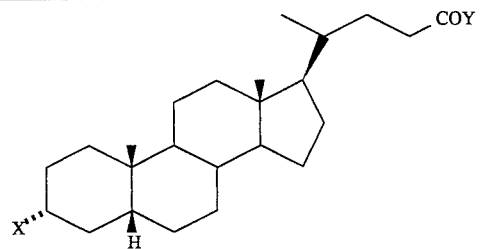

| | | |
|---|---|---|
| 19 | H | spermine |
| 20 | H | NHCH$_2$CH$_2$CH$_2$CH$_2$NH$_2$ |
| 21 | H | NHCH$_2$CH$_2$NHCH$_2$CH$_2$NHCH$_2$CH$_2$NH$_2$ |
| 22 | OSO$_3$H | spermine |
| 23 | OSO$_3$H | NHCH$_2$CH$_2$CH$_2$CH$_2$NH$_2$ |
| 24 | OSO$_3$H | NHCH$_2$CH$_2$NHCH$_2$CH$_2$NHCH$_2$CH$_2$NH$_2$ |
| 25 | OH | spermine |
| 26 | OH | NHCH$_2$CH$_2$CH$_2$CH$_2$NH$_2$ |
| 27 | OH | NHCH$_2$CH$_2$NHCH$_2$CH$_2$NHCH$_2$CH$_2$NH$_2$ |

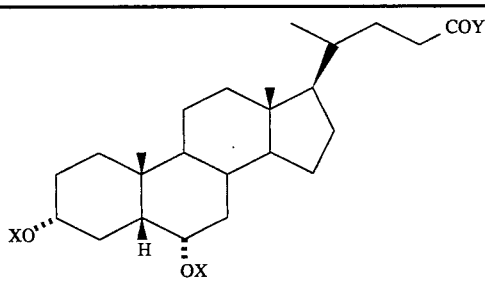

6

-continued

| Compound | X | Y |
|---|---|---|
| 28 | H | spermine |
| 29 | SO$_3$H | spermine |
| 30 | H | NHCH$_2$CH$_2$CH$_2$CH$_2$NH$_2$ |
| 31 | SO$_3$H | NHCH$_2$CH$_2$CH$_2$CH$_2$NH$_2$ |
| 32 | H | NHCH$_2$CH$_2$NHCH$_2$CH$_2$NHCH$_2$CH$_2$NH$_2$ |
| 33 | SO$_3$H | NHCH$_2$CH$_2$NHCH$_2$CH$_2$NHCH$_2$CH$_2$NH$_2$ |

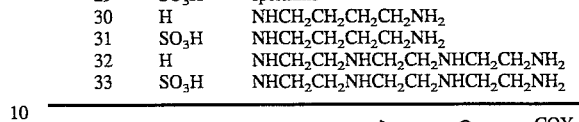

| | | |
|---|---|---|
| 34 | H | spermine |
| 35 | SO$_3$H | spermine |
| 36 | H | NHCH$_2$CH$_2$CH$_2$CH$_2$NH$_2$ |
| 37 | SO$_3$H | NHCH$_2$CH$_2$CH$_2$CH$_2$NH$_2$ |
| 38 | H | NHCH$_2$CH$_2$NHCH$_2$CH$_2$NHCH$_2$CH$_2$NH$_2$ |
| 39 | SO$_3$H | NHCH$_2$CH$_2$NHCH$_2$CH$_2$NHCH$_2$CH$_2$NH$_2$ |

Individual compounds according to the present invention may be synthesized using the appropriate of three protocols. For example, Compounds such as 1 and 2 may be synthesized according to the following protocol using 23,24-bisnor-5-cholenic acid-3-β-ol as the starting material:

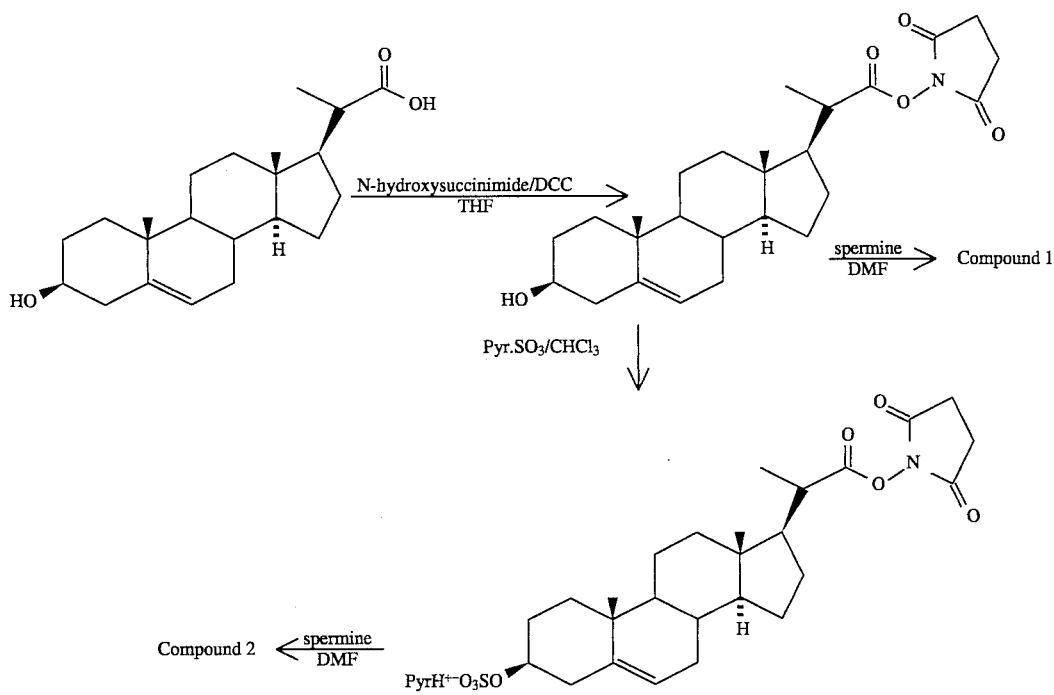

More specifically, compounds 1 and 2 were prepared according to the following examples.

EXAMPLE I

The 23,24-Bisnor-3β-ol-5-cholenic Acid N-Hydroxylsuccinimidyl ester shown in the above protocol was synthesized by adding, dropwise, a solution that was prepared from dicyclohexylcarbodiimide (419 mg, 2.04 mmol) plus 5 ml of tetrahydrofuran (THF) to a stirred mixture of 23, 24-bisnor-5-cholenic acid-3β-ol (702 mg, 2.03 mmol) and N-hydroxysuccinimide (235 mg, 2.0 mmol) that was suspended in 30 ml of anhydrous THF maintained at 50° C. The reaction mixture was stirred for an additional 3 hours at 50° C., and left overnight at ambient temperature. The supernatant was separated from the product mixture by filtration and concentrated under reduced pressure. The solid residue that resulted was then dissolved in 40 ml of chloroform and washed, sequentially, with saturated sodium bicarbonate (20 ml), water (20 ml), and brine (10 ml). The chloroform solution was then dried over anhydrous sodium sulfate and concentrated under reduced pressure. Recrystallization from acetone/petroleum ether gave 577 mg (64%) of 23,24-bisnor-3β-ol-5-cholenic acid N-hydrosylsuccinimidyl ester as a colorless powder, having a melting point of 214°–216° C.

Compound 1, the 23,24-Bisnor-3β-ol-5-cholenic acid 3-ol spermine conjugate, was prepared according to the following example II.

EXAMPLE II

To a stirred solution of spermine (68 mg, 0.34 mmol) in 1 ml of anhydrous chloroform was added, dropwise, a solution prepared from 23,24-bisnor-3β-ol-cholenic acid N-hydroxylsuccinimidyl ester (86 mg, 0.19 mmol) plus 4 ml of chloroform over a 5 minute period at ambient temperature. After 30 minutes of reaction, some precipitate appeared in the flask. The heterogenous mixture was stirred overnight, and then transferred to a test tube and washed, sequentially, with 0.1M NaOH (1×2 ml), water (1×2 ml), and saturated sodium chloride (1×1 ml). After drying over anhydrous potassium carbonate and subsequent solvent removal under reduced pressure, 84 mg of crude product was obtained. Subsequent chromatographic purification using 3.0 g of EM Science silica gel, eluting first with CH$_3$OH and then with CH$_3$OH/30% NH$_4$OH (4/1, v/v), afforded 42 mg of pure product.

Pyridium 23,24-bisnor-3β-ol-5-cholenic Acid N-hydroxysuccinimidyl ester 3-sulfate was prepared according to the following example.

EXAMPLE III

To a solution of 23,24-bisnor-3β-ol-5-cholenic acid N-hydrosylsuccinimidyl ester (445 mg, 1.00 mmol) in 20 ml of anhydrous chloroform was added, in a single portion, 481 mg (3.03 mmol) of sulfur trioxide/pyridine complex. After stirring the heterogenous mixture for 14 hours at ambient temperature, an additional 20 ml of chloroform was then added, and the mixture cooled to about −10° C., and filtered. Concentration of the flitrate under reduced pressure, followed by recrystallization from acetone/petroleum ether, afforded 355 mg (75%) of Pyridium 23,24-bisnor-3β-ol-5-cholenic Acid N-hydroxysuccinimidyl ester 3-sulfate as colorless crystals having a melting point of 220°–224° C. (dec).

Compound 2, the 23,24-bisnor-3β-ol-5-cholenic acid 3-sulfate spermine conjugate was prepared according to the following example.

EXAMPLE IV

To a stirred solution of spermine (215 mg, 1.06 mmol) in 15 ml of anhydrous DMF, which was maintained at 0° C., was added a solution of pyridinium 23,24-bisnor-3β-ol-5-cholenic acid N-hydroxysuccinimidyl ester 3-sulfate (380 mg, 0.63 mmol) in 2.5 ml of anhydrous DMF over a 20 minute period. The mixture was then stirred at ambient temperature for 1 hour, quenched with 20 ml of 0.1M NaOH, and extracted with 1-butanol (2×20 ml). The combined extracts were washed with water (3×20 ml) and brine (2×20 ml) and dried over sodium sulfate. Removal of solvent under reduced pressure (45° C.) afforded 218 mg of solid residue, which was then purified by column chromatography (4.5 g EM Science silica gel, CH$_3$OH/30% NH4OH (4/1, v/v)), and filtration (0.45 μm Millipore) to give 140 mg (35%) of compound 2 as a cream-colored solid having a melting point of 212–221 (dec).

Compounds such as compound 7 may be synthesized according to the following protocol using deoxycholic acid as the starting material:

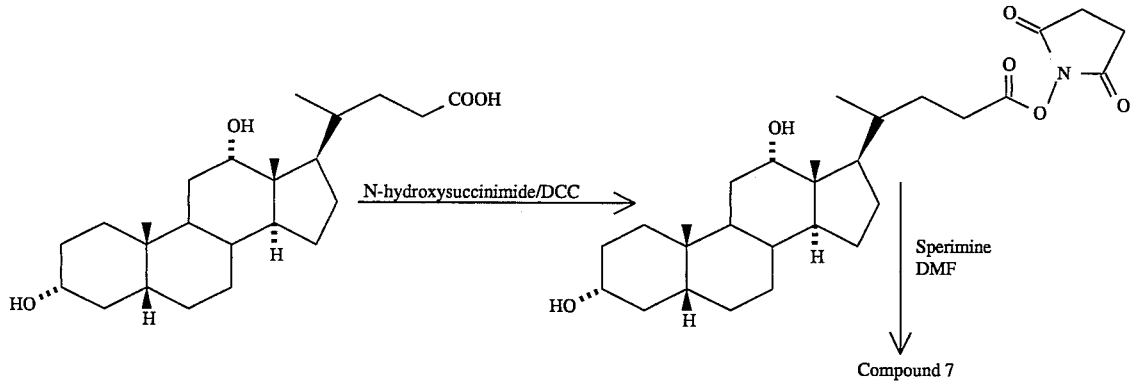

Compound 7

The N-hydroxylsuccinimidyl ester of deoxycholic acid used in the synthesis of compound 7 was prepared in accordance with the following example.

EXAMPLE V

Deoxycholic acid (7.86 g, 20.0 mmol) and N-hydroxysuccinimide (2.38 g, 20.7 mmol) were partially dissolved in 100 ml of anhydrous tetrahydrofuran and then added to a stirred solution that was prepared from dicyclohexylcarbodiimide (4.80 g, 23.3 mmol) plus 20 ml of tetrahydrofuran. The reaction mixture was stirred for an additional 3.5 hours and the dicyclohexyl urea removed by filtration. After the dicyclohexyl urea was washed with tetrahydrofuran, the combined flitrate was concentrated under reduced pressure to about one-third of its initial volume. Chloroform (150 ml) was then added, and the resulting solution was washed with saturated aqueous sodium bicarbonate (2×100 ml), water (1×100 ml), and saturated sodium chloride (1×50 ml). After drying with anhydrous sodium sulfate, the solvent was removed under reduced pressure, and the residue was recrystallized from ethyl acetate/hexanes to give 7.08 g of product in the form of a colorless powder, and having a melting point of 167°–169° C.

Compound 7, the deoxycholic acid-spermine conjugate was synthesized according to the following example.

EXAMPLE VI

To a stirred solution of spermine (241 mg, 1.19 mmol) in 4 ml of anhydrous $CH_2Cl_2$ was added, over the course of 5 minutes at ambient temperature, a solution that was prepared from the N-hydroxylsuccinimidyl ester of deoxycholic acid (351 mg, 0.71 mmol) 4 ml of $CH_2Cl_2$, and 2 ml of tetrahydrofuran. During this addition, a colorless precipitate appeared, and an additional 4 ml of anhydrous chloroform was added to the reaction mixture. The heterogenous mixture was stirred at ambient temperature overnight, and the solvent was then removed under reduced pressure. The residue was then dissolved in 8 ml of chloroform. The resulting solution was placed in 2 test tubes and these were washed with 0.1M NaOH (1×2 ml), water (1×2 ml), and saturated sodium chloride (1 ml). In order to assist phase separation, the mixtures were subjected to centrifugation. The resulting organic phase was then dried over anhydrous potassium carbonate and concentrated under reduced pressure to give 320 mg of solid residue. Subsequent chromatography (5 g of EM Silica gel), using $CH_3OH/30\% NH_4OH$ (3/2, v/v) as the eluent afforded 255 mg of product which was solidified on drying.

Compounds such as compound 13 may be synthesized according to the following protocol using cholic acid as the starting material:

that was prepared from dicyclohexylcarbodiimide (4.22 g, 20.5 mmol) and 20 ml of tetrahydrofuran. The mixture was stirred at ambient temperature for 3 hours, and then allowed to stand overnight. The resultant supernatant was concentrated under reduced pressure, and the residue dissolved in 200 ml of chloroform. The solution was then washed with saturated sodium carbonate (2×200 ml), water (1×100 ml), and saturated sodium chloride (1×50 ml). After drying with anhydrous sodium sulfate and solvent removal under reduced pressure, 9.1 g of crude product was obtained which was used without further purification.

Compound 13, the cholic acid-spermine conjugate was synthesized according to the following example.

EXAMPLE VIII

To a stirred solution of spermine (196 mg, 0.97 mmol) in 2 ml of anhydrous chloroform was added, over the course of 5 minutes at ambient temperature, a solution prepared from the N-hydroxysuccinimidyl ester of cholic acid (402 mg, 0.59 mmol) plus 4 ml of chloroform. The homogeneous mixture was then stirred overnight, transferred to two test tubes, and washed with 0.1M NaOH (1×2 ml), water (1×2 ml), and saturated sodium chloride (1 ml). After drying with anhydrous potassium carbonate, the solvent was removed under reduced pressure to give 88 mg of crude product. Subsequent purification using 2.0 g of silica, and $CH_3OH/30\% NH_4OH$ (3/2, v/v) as the eluting solvent, afforded 55 mg of the desired conjugate in the form of a colorless, foam-like solid.

The remainder of the compounds according to the present invention may be synthesized using similar protocols with the appropriate starting material having the similar steroidal structure as found in the desired end-product compound.

The antimicrobial activity of the compounds according to the present invention were compared with the results obtained for squalamine as reported in Proc. Nat. Acad. Sci. USA 90:1354 (1993), supra, the disclosure of which is incorporated in toto herein. The data reported in Table 1 is the minimum inhibitory concentration (MIC) required for

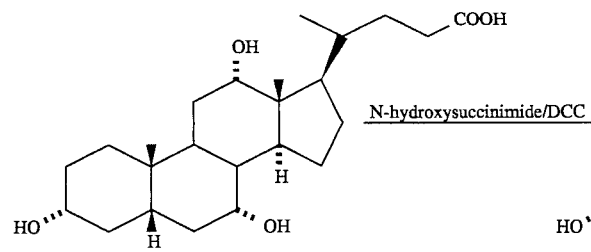
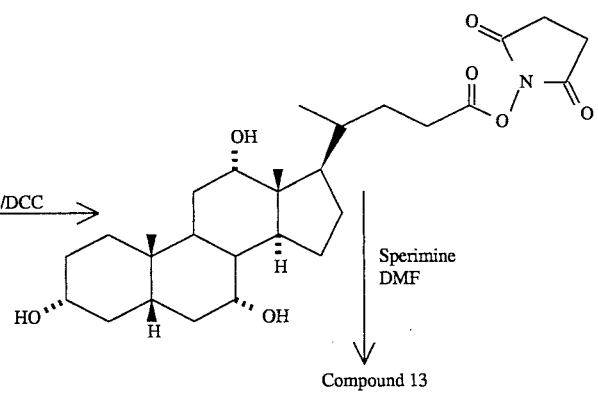

Compound 13

The N-hydroxylsuccinimidyl ester of cholic acid used as the intermediate in the preparation of compound 13 was synthesized according to the following example.

EXAMPLE VII

To a stirred solution prepared from cholic acid (8.18 g, 20.0 mmol) and N-hydroxysuccinimide (2.7 g, 23.5 mmol) in 80 ml of anhydrous tetrahydrofuran was added a solution complete inhibition of microbial growth. The MIC was determined utilizing known micro-broth dilution methods in which inocula of $10^6$/ml of the test organism were incubated in 0.5X trypticase soy broth at 35° C. for 24 hours. The MIC assay data reported in Table 1 is considered by scientists to be an accurate indication for the therapeutic potential of compounds tested when used to treat microbial diseases in animals, particularly in mammals.

| Conjugate | ANTIMICROBIAL ACTIVITY (MIC) (μg/ml) | | | | | | |
|---|---|---|---|---|---|---|---|
| | E. coli (25922) | Pseudomonas aeruginosa (27853) | Staphylococcus aureus (29123) | Proteus vulgaris (13315) | Serratia marcescens (8100) | Candida albicans (14053) | $K_{50}$ |
| Squalamine[c] | 1–2 | 4–8 | 1–2 | 4–8 | >125 | 4–8 | >100 |
| 1 | 12.5 | 1.56 | 6.25 | 25 | >100[a] | 12.5 | >100 |
| 2 | 6.25 | 3.13 | >100 | >100 | >100[a] | 12.5[b] | >100 |
| 3 | >100 | >100 | >100 | >100 | >100[a] | >100[b] | >100 |
| 5 | >100 | 25 | 100 | >100 | >100[a] | >100[b] | >100 |
| 7 | 3.13 | 3.13 | 1.56 | 3.13 | 25[a] | 3.13[b] | 12.5 |
| 9 | 50 | 100 | 25 | 50 | >100[a] | 25[b] | 50 |
| 11 | 12.5 | 6.25 | 12.5 | 25 | 50[a] | 12.5[b] | 25 |
| 13 | 25 | 25 | 12.5 | 100 | >100[a] | 25[b] | >100 |
| 14 | 12.5 | 3.13 | 6.25 | 25 | >100[a] | 100[b] | ND |
| 15 | >100 | >100 | 100 | >100 | >100[a] | >100[b] | >100 |
| 17 | 50 | 50 | 25 | 50 | >100[a] | 25[b] | 100 |

[a] represents ATCC No. 13880;
[b] represents ATCC No. 90028;
[c] reports on the data from the Proc. Natl. Acad. Sci., supra, as the compound was not available to be directly compared with the remainder of the compounds reported herein; and
ND indicates the assay was not done $K_{50}$ as used in the above table represents the concentration of compound that is required to induce the release of 50% of the hemoglobin that is contained with $3\times10^7$ sheep red blood cells at 37° C. after a 60 minute period [specific protocols for these tests were similar to those reported in Biochem. Pharm. 37:827 (1988)]. The numbers in parentheses correspond to accession numbers with the American Type Culture Collection. In addition to the results reported in the Table, compound 2 was also tested against clinical isolates of *Cryptococcus neoformans* and *Aspergillus fumigatus* and gave MIC values of 3.13 and 12.5 μg/ml, respectively.

As evidenced by the data in Table 1, the compounds according to the present invention exhibit potent antimicrobial activity against a broad spectrum of microorganisms.

The compounds according to the present invention, based upon the scientifically recognized correlation between the assays reported in Table 1 and the therapeutic activity that can be expected when these compounds are administered to mammals, are potentially useful in the treatment of microbial disease states in mammals when administered to the mammal in need of therapy in amounts of from about 1 mg to about 100 mg per kg of body weight per day. Of course, the exact dose levels given on a daily basis is meant to be adapted by the physician to provide the optimum therapeutic response. For example, several divided doses may be administered daily, or the dose may be proportionally increased or reduced as indicated by the exigencies of the individual therapeutic situation. The compounds according to the present invention may be administered as the free compound, or as a pharmaceutically acceptable salt thereof, or as an active agent in a pharmaceutical formulation that includes such carriers, fillers, extenders, dispersants, creams, gels and solutions as is common in the pharmaceutical formulatory arts. The compounds according to the present invention may be formulated for all modes of application including, for example, modes that encompass topical, intravenous, oral, intraperitoneal, subcutaneous, vaginal, ocular or intramuscular routes of administration. These modes may be, for example, in the form of capsules, powders, tablets, gels, creams, ointments, or liquids for injection or topical application. In addition the compounds according to the present invention may be compounded with other medicaments, or used in conjunction with devices such as, for example, condoms for use in vaginal application.

Thus while I have illustrated and described the preferred embodiment of my invention, it is to be understood that this invention is capable of variation and modification, and I therefore do not wish to be limited to the precise terms set forth, but desire to avail myself of such changes and alterations which may be made for adapting the invention to various usages and conditions. Thus, such variations and modifications are properly intended to be within the full range of equivalents, and therefore within the purview of the following claims.

Having thus described my invention and the manner and a process of making and using it in such full, clear, concise and exact terms so as to enable any person skilled in the art to which it pertains, or with which it is most nearly connected, to make and use the same;

I claim:

1. A sterol conjugate compound of the formula

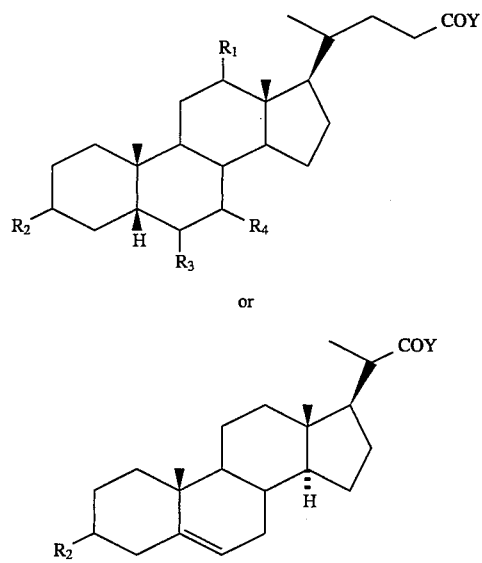

wherein each $R_1$, $R_2$, $R_3$ and $R_4$ is individually selected from the group consisting of H, OH and $OSO_3H$; and wherein Y is $NH(CH_2)_3NH(CH_2)_4NH(CH_2)_3NH_2$, $NHCH_2CH_2CH_2CH_2CH_2NH_2$, or $NHCH_2CH_2NHCH_2CH_2NHCH_2CH_2NH_2$.

2. A compound according to claim 1 which is

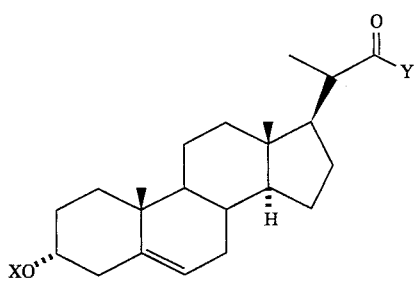

wherein Y is selected from the group consisting of NH(CH₂)₃NH(CH₂)₄NH(CH₂)₃NH₂, NHCH₂CH₂CH₂CH₂NH₂, and NHCH₂CH₂NHCH₂CH₂NHCH₂CH₂NH₂, and wherein X is selected from the group consisting of H and SO₃H.

3. A compound according to claim 2 wherein Y is NH(CH₂)₃NH(CH₂)₄NH(CH₂)₃NH₂.
4. The compound according to claim 3 wherein X is H.
5. The compound according to claim 3 wherein X is SO₃H.
6. A compound according to claim 2 wherein Y is NHCH₂CH₂CH₂CH₂NH₂.
7. The compound according to claim 6 wherein X is H.
8. The compound according to claim 6 wherein X is SO₃H.
9. A compound according to claim 2 wherein Y is NHCH₂CH₂NHCH₂CH₂NHCH₂CH₂NH₂.
10. The compound according to claim 9 wherein X is H.
11. The compound according to claim 9 wherein X is SO₃H.
12. The compound according to claim 1 which is

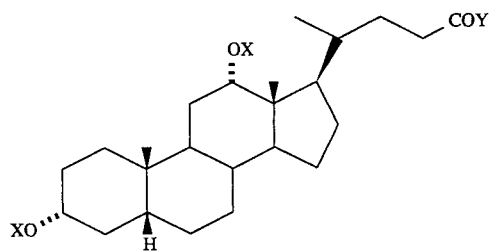

wherein Y is selected from the group consisting of NH(CH₂)₃NH(CH₂)₄NH(CH₂)₃NH₂, NHCH₂CH₂CH₂CH₂CH₂NH₂, and NHCH₂CH₂NHCH₂CH₂NHCH₂CH₂NH₂, and wherein X is selected from the group consisting of H and SO₃H.

13. The compound according to claim 1 which is

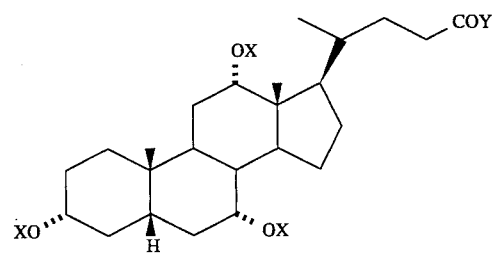

wherein Y is selected from the group consisting of NH(CH₂)₃NH(CH₂)₄NH(CH₂)₃NH₂, NHCH₂CH₂CH₂CH₂NH₂, and NHCH₂CH₂NHCH₂CH₂NHCH₂CH₂NH₂, and wherein X is selected from the group consisting of H and SO₃H.

14. The compound according to claim 1 which is

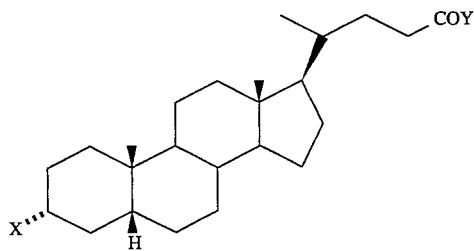

wherein X is selected from the group consisting of H, OSO₃H, and OH, and Y is selected from the group consisting of NH(CH₂)₃NH(CH₂)₄NH(CH₂)₃NH₂, NHCH₂CH₂CH₂CH₂NH₂, or NHCH₂CH₂NHCH₂CH₂NHCH₂CH₂NH₂.

15. A compound according to claim 1 which is

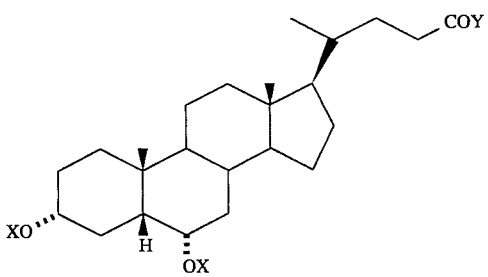

wherein Y is selected from the group consisting of NH(CH₂)₃NH(CH₂)₄NH(CH₂)₃NH₂, NHCH₂CH₂CH₂CH₂NH₂, and NHCH₂CH₂NHCH₂CH₂NHCH₂CH₂NH₂, and wherein X is selected from the group consisting of H and SO₃H.

16. A compound according to claim 1 which is

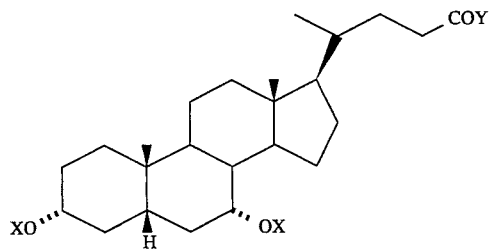

wherein Y is selected from the group consisting of NH(CH₂)₃NH(CH₂)₄NH(CH₂)₃NH₂, NHCH₂CH₂CH₂CH₂NH₂, and NHCH₂CH₂NHCH₂CH₂NHCH₂CH₂NH₂, and wherein X is selected from the group consisting of H and SO₃H.

* * * * *